United States Patent [19]

Peake et al.

[11] 4,201,780
[45] * May 6, 1980

[54] MONO-5-SUBSTITUTED-3-CHLORO-4H-1,2,6-THIADIAZIN-4-ONE ANTIFUNGAL AGENTS

[75] Inventors: Clinton J. Peake; Wayne N. Harnish, both of Medina; Bruce L. Davidson, Middleport, all of N.Y.

[73] Assignee: FMC Corporation, Philadelphia, Pa.

[*] Notice: The portion of the term of this patent subsequent to Jun. 27, 1995, has been disclaimed.

[21] Appl. No.: 894,980

[22] Filed: Apr. 10, 1978

Related U.S. Application Data

[63] Continuation-in-part of Ser. No. 782,860, Mar. 30, 1977, Pat. No. 4,097,594.

[51] Int. Cl.² .................... C07D 285/16; A01N 9/12
[52] U.S. Cl. ........................................ 424/246; 544/8
[58] Field of Search ............................ 424/246; 544/8

[56] References Cited

FOREIGN PATENT DOCUMENTS 854184 11/1977 Belgium .

OTHER PUBLICATIONS

Geevers et al., Rec. Trav. Chim., vol. 93, pp. 270-272 (1974).

Primary Examiner—John M. Ford
Attorney, Agent, or Firm—Harrison H. Young, Jr.; H. Robinson Ertelt

[57] ABSTRACT

Selected mono-5-substituted-3-chloro-4H-1,2,6-thiadiazin-4-ones having the general formula

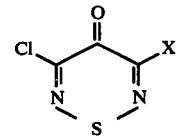

are described which are useful for control of fungal disease in plants.

3 Claims, No Drawings

MONO-5-SUBSTITUTED-3-CHLORO-4H-1,2,6-THIADIAZIN-4-ONE ANTIFUNGAL AGENTS

STATEMENT OF RELATED APPLICATION

This application is a Continuation in Part of copending U.S. application Ser. No. 782,860, Filed Mar. 30, 1977, now U.S. Pat. No. 4,097,594.

BACKGROUND OF THE INVENTION

The present invention relates to a method for controlling fungal disease in plants, to novel antifungal compositions, and to compounds useful for controlling fungi which attack agricultural and garden plants and seeds. More particularly, the invention relates to the use of a selected mono-5-substituted-3-chloro-4H-1,2,6-thiadiazin-4-one as an antifungal agent for controlling fungal disease in plants.

Geevers and Trompen disclosed the preparation 3,5-dichloro-4H-1,2,6-thiadiazin-4-one and its use as an intermediate to prepare various other 5-substituted-3-chloro-4H-1,2,6-thiadiazin-4-ones including, interalia, the 5-chloro and 5-phenoxy derivatives. J. Geevers and W. P. Trompen, *Rec. Trav. Chim.*, 93, 270 (1974). The 5-phenylthio derivatives are disclosed in U.S. Patent Application Ser. No. 782,816 filed Mar. 30, 1977.

While 5-chloro and 5-phenoxy derivatives and the method for preparing them have been disclosed, the Geevers and Trompen article provides no indication of any biological activity. More particularly, there is no suggestion that the compounds of this invention have antifungal activity.

It has now been found that selected mono-5-substituted-3-chloro-4H-1,2,6-thiadiazin-4-ones, which are hereinafter described, exhibit excellent antifungal activity and are useful in providing control of fungal disease in agricultural crops by foliar, seed, and soil application.

SUMMARY OF THE INVENTION

The present invention thus provides (1) a method for controlling fungal disease in plants which comprises applying a selected mono-5-substituted-3-chloro-4H-1,2,6-thiadiazin-4-one, as defined below, to the locus where control is desired, (2) antifungal compositions for control of fungal disease in plants, and (3) novel compounds which are useful for control of fungi.

DETAILED DESCRIPTION

In accordance with a first aspect of the present invention, there is provided a method for controlling fungal disease in agricultural crops and other plants which comprises applying to the locus where control is desired an effective fungistatic or fungicidal amount of a mono-5-substituted-3-chloro-4H-1,2,6-thiadiazin-4-one of the formula

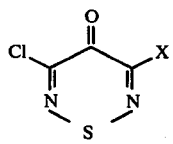

I in which X is phenoxybenzyloxy, α-cyano-phenoxybenzyloxy, methylenedioxyphenoxy optionally substituted on the methylene with 1 or 2 lower alkyl groups, 2,3-dihydrobenzofuranyloxy optionally substituted at the 2 or 3 position of the furanyl ring with 1 or 2 lower alkyl groups, phenylseleno in which the phenyl ring is optionally substituted with 1 to 3 groups independently selected from lower alkyl and halogen, or substituted phenoxy having the formula

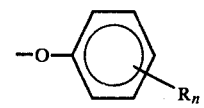

II wherein n has a value of 1 to 3 inclusive, wherein at least one R group is halo(lower)alkyl, hydroxy(lower)alkyl, carboxyethenyl, lower alkoxycarbonylethenyl, dimethylamino, lower alkylamino($C_{1-2}$) alkyl, lower alkylaminocarbonyloxy($C_{1-2}$)alkyl, or phenylaminocarbonyloxy($C_{1-2}$)alkyl, and wherein the remaining R groups are independently selected from lower alkyl, halo, lower alkoxy, hydroxy, nitro, cyano, amino, carboxyl, lower alkanoyl, lower alkanoyl acylamino, lower alkoxycarbonyl, carboxy(lower)alkyl, lower alkylureido, phenylureido, trihalomethyl, cyano(lower)alkyl, phenyl(lower)alkoxycarbonyloxy, lower alkylaminocarbonyloxy, phenylaminocarbonyloxy, lower alkylthio, lower alkylsulfinyl and lower alkylsulfonyl.

Unless it is otherwise indicated, the term "lower" means having 1 to 6 carbon atoms, straight or branched chain, preferably 1 to 4 carbon atoms, and the term "halogen" means bromine, chlorine and fluorine or iodine.

In the method of this invention an effective fungistatic or fungicidal amount of active ingredient is applied to foliage or seeds of agricultural plants or to the soil in which the plants are growing or are to be planted, i.e., the locus where control is desired. When so applied, the compounds prevent fungal infection or inhibit further development of a pre-existing fungal disease.

The selected antifungal agent may be applied as the technical material, or as a formulated product. Typical formulations include the antifungal agent in combination with an agriculturally acceptable carrier, preferably with a surface active agent, and optionally with other active ingredients. Suitable formulations include granules, powders, or liquids, the choice varying with the fungus and environmental factors present at the particular locus of infestation. Thus, the compounds may be formulated as granules of various sizes, as dusts, as wettable powders, as emulsifiable concentrates, as solutions, as dispersions, as controlled release compositions, and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of about 0.5% up to about 99.5% by weight of the formulation. Additives and carriers may comprise about 99.5% by weight to as low as about 0.5% by weight of the formulation. Surface active agents, if employed in the formulation, may be present at various concentrations, suitably in the range of 1% to 30% by weight.

The formulation may be used as such or diluted to a desired use dilution with a suitable diluent or carrier. The concentration of the active ingredient in use dilution is normally in the range of about 0.001% to about 4% by weight. Many variations of spraying, dusting, soil-incorporation may be utilized in applying the compounds. The compounds may be applied as an ingredient of compositions used in the art by substituting or adding a compound of this invention to such compositions.

The antifungal agents of this invention may be formulated and applied with other compatible active ingredients, including nematicides, insecticides, acaricides, other fungicides, plant growth regulators, herbicides, fertilizers, etc.

In applying the foregoing chemicals, whether alone or with other agricultural chemicals, an effective fungistatic or fungicidal amount of the active ingredient must be applied. While the application rate will vary widely depending on the choice of compound, the formulation and mode of application, the plant species being protected, and the planting density, a suitable use rate may be in the range of 0.05 to 5 kg/hectare, preferably 0.5 to about 4 kg/hectare.

The antifungal compound of this invention comprises a compound of formula I as defined above, and the fungicidal compositions comprise the compound of the invention in admixture with an agriculturally acceptable carrier, preferably containing a compatible surface active agent.

The compounds of this invention are in general prepared according to the teaching of Geevers and Trompen, supra; that is, by reacting 3,5-dichloro-4H-1,2,6-thiadiazin-4-one with alcoholate ions, for example a compound of the formula MX where M is an alkali or alkaline earth metal, preferably sodium or potassium, and X is as defined above. The following examples are typical of the preparation of the compounds.

EXAMPLE 1

Synthesis of 3,5-Dichloro-4H-1,2,6-thiadiazin-4-one

A 50 ml flask was charged with 20 ml formic acid. The flask was purged with a stream of dry nitrogen. The nitrogen purge was continued while 6.3 g 3,4,4,5-tetrachloro-4H-1,2,6-thiadiazinone was added dropwise over 0.5 hour during which the temperature of the reaction mixture was maintained at 10°±1° C. Following addition the reaction mixture was stirred at 10° C. for 2 hours then at room temperature for 64 hours, then poured into 60 ml. ice-water with stirring. The resulting mixture was filtered and the filter cake washed with water and dried to yield 2.2 g of pale yellow 3,5-dichloro-4H-1,2,6-thiadiazin-4-one, mp 81°–82° C.

EXAMPLE 2

Synthesis of 3-Chloro-5-phenoxy-4H-1,2,6-thiadiazin-4-one

A sodium phenoxide solution was prepared by adding 1.0 g of sodium hydroxide to 2.4 g phenol in 25 ml of warm, distilled water. This mixture was stirred for 5 minutes then added to a suspension of 4.6 g of finely ground 3,5-dichloro-4H-1,2,6-thiadiazin-4-one in 75 ml of distilled water in a 250 ml flask. This addition required 15 minutes during which the temperature rose to 32° C. After being stirred at room temperature for one hour, the orange mixture was filtered, and the filter cake was washed with water. Recrystallization from 100 ml of ethanol yielded 4.2 g of fluffy, pale yellow needles of 3-chloro-5-phenoxy-4H-1,2,6-thiadiazin-4-one, mp 121°–123° C.

EXAMPLE 3

Synthesis of 3-Chloro-5[(4-hydroxymethyl)phenoxy]-4H-1,2,6-thiadiazin-4-one

To a stirred suspension of 18.3 grams (0.10 mole) of 3,5-dichloro-4H-1,2,6-thiadiazin-4-one in 400 ml of water was added dropwise a previously prepared solution of 12.4 grams (0.10 mole) of 4-hydroxybenzyl alcohol in 100 ml of aqueous 1 N sodium hydroxide. The mildly exothermic reaction mixture was stirred for 3 hours at ambient temperature. A yellow-orange precipitate was collected by vacuum filtration and washed with water. The filter cake was dried and recrystallized from hot chlorobenzene to give in two crops, 17.6 grams (65%) of 3-chloro-5-[(4-hydroxymethyl)-phenoxy]-4H-1,2,6-thiadiazin-4-one; m.p. 151°–152.5° C.

EXAMPLE 4

Synthesis of 3-[(4-bromomethyl)phenoxy]-5-chloro-4H-1,2,6-thiadiazin-4-one

To a stirred mixture of 5.0 grams (0.018 mole) of 3-chloro-5-(4-hydroxymethyl)phenoxy-4H-1,2,6-thiadiazin-4-one in 115 ml of chloroform was added dropwise 1.83 grams (0.007 mole) of phosphorus tribromide in 20 ml of chloroform. The reaction mixture was stirred at ambient temperature for 2 hours, then 100 ml of water was added. The organic layer was separated and dried with magnesium sulfate. The mixture was filtered and the filtrate evaporated under reduced pressure to a solid residue. The solid was recrystallized from methylcyclohexane and toluene to give 4.6 grams (75%) of 3-[(4-bromomethyl)phenoxy]-5-chloro-4H-1.2,6-thiadiazin-4-one; mp 140.5°–142.5° C.

EXAMPLE 5

Synthesis of 3-Chloro-5-[4-(N-methylcarbamoyloxymethyl)phenoxy]-4H-1,2,6-thiadiazin-4-one To a stirred mixture of 5.0 grams (0.018 mole) of 3-chloro-5-(4-hydroxymethyl)phenoxy-4H-1,2,6-thiadiazin-4-one in 125 ml of chloroform was added 2 drops of dibutyltin diacetate, then a solution of 1.1 grams (0.018 mole) of methyl isocyanate in 40 ml of chloroform. The reaction mixture was stirred at ambient temperature for 24 hours, then evaporated under reduced pressure to a residual oil. Higher boiling volatiles were removed by evaporation under high vacuum. The residual oil was triturated with ethanol to give a yellow solid. The solid was recrystallized from 25 ml of hot ethanol to give 4.0 grams (65.2%) of 3-chloro-5-[4-(N-methylcarbamoyloxymethyl)phenoxy]-4-H-1,2,6-thiadiazin-4-one; mp 103°–104.5° C.

EXAMPLE 6

Synthesis of 3-[4-(2-carboxyethenyl)phenoxy]-5-chloro-4H-1,2,6 thiadiazin-4-one

To a stirred suspension of 14.6 grams (0.08 mole) of 3,5-dichloro-4H-1,2,6-thiadiazin-4-one in 350 ml of water was added dropwise a previously prepared solution of 13.1 grams (0.08 mole) of p-hydroxycinnamic acid in 80 ml of aqueous 1 N sodium hydroxide. The reaction mixture was stirred for 2 hours at ambient temperature, then acidified with aqueous 6 N hydrochloric acid. A yellow precipitate was collected by vacuum filtration and washed with water, then dried for 5 hours/50° C. The solid was triturated with hot ethanol and collected by vacuum filtration, to give 23.3 grams (93.8%) of 3-[4-(2-carboxyethenyl)phenoxy]-5-chloro-4H-1,2,6-thiadiazin-4-one; m.p. >280° C. The nmr and the ir spectra were consistent with the proposed structure.

Analyses calc'd for $C_{12}H_7ClN_2O_4S$: C 46.38; H 2.27; N 9.01; Found: C 46.41; H 2.50; N 8.91.

EXAMPLE 7

Synthesis of 3-chloro-5-[4-(2-ethoxycarbonylethenyl)phenoxy]-4H-1,2,6-thiadiazin-4-one A stirred solution of 15.5 grams (0.05 mole) of 3-[4-(2-carboxyethenyl)phenoxy]-5-chloro-4H-1,2,6-thiadiazin-4-one in 150 ml of thionyl chloride was heated under reflux for 16 hours, then allowed to cool to ambient temperature. The excess thionyl chloride was removed under reduced pressure to give a residual solid. The solid was dissolved in 300 ml of methylene chloride. To the resulting solution was carefully added 6.1 grams (0.06 mole) of triethylamine; then, dropwise, 4.6 grams (0.1 mole) of absolute ethanol. The reaction mixture was stirred at ambient temperature for 2.5 hours, then diluted with 150 ml of water. The organic layer was separated and washed with 200 ml of water, then 150 ml of an aqueous solution saturated with sodium chloride. The organic layer was dried with magnesium sulfate and filtered. The filtrate was evaporated under reduced pressure to a solid residue. The solid was recrystallized twice with ethanol to give 8.7 grams (51%) of 3-chloro-5-[4-(2-ethoxycarbonylethenyl)phenoxy]-4H-1,2,6-thiadiazin-4-one; mp 126°-127.5° C.

EXAMPLE 8

Synthesis of 3-chloro-5-(α-cyano-3-phenoxybenzyloxy)-4H-1,2,6 thiadiazin-4-one

To a stirred solution of 7.3 grams (0.04 mole) of 3,5-dichloro-4H-1,2,6-thiadiazin-4-one and 9.0 grams (0.04 mole) of a α-cyano-3-phenoxybenzyl alcohol in 130 ml of ethyl acetate was added dropwise a solution of 4.1 grams (0.04 mole) of triethylamine in approximately 40 ml of ethyl acetate. Upon complete addition the reaction mixture was stirred at ambient temperature for 16 hours, then diluted with 100 ml of water to dissolve triethylamine hydrochloride. The organic layer was removed and washed with 100 ml of water, then with 100 ml of an aqueous solution saturated with sodium chloride. The organic layer was dried with magnesium sulfate and filtered. The filtrate was evaporated under reduced pressure to a residual solid. The solid was triturated with absolute ethanol and collected by filtration. The filter cake was washed with hexane and recrystallized from glacial acetic acid. The yield was 5.8 grams (39%) of 3-chloro-5-(α-cyano-3-phenoxybenzyloxy)-4H-1,2,6-thiadiazin-4-one; m.p. 146.5°-147.7° C. The nmr and the ir spectra were consistent with the proposed structure.

Analyses calc'd for $C_{17}H_{10}ClN_3O_3S$: C 54.91; H 2.71; N 11.30; Found: C 55.02; H 3.07; N 10.93.

The compounds shown in the following examples have been similarly prepared.

| Example | Identity of X | mp (°C.) |
|---|---|---|
| 9 | 4-(2-hydroxyethyl)phenoxy | 144.5–145.5 |
| 10 | 4-(N-phenylaminocarbonyloxy)-phenoxy | 120.5–121.5 |
| 11 | 4-(N-ethylaminocarbonyloxy)-phenoxy | 145.5–146.5 |
| 12 | 4-(N-butylaminocarbonyloxy)-phenoxy | 110.5–112 |
| 13 | 4-dimethylaminophenoxy | 135.5–136.5 |
| 14 | 2,3-dihydro-2,2-dimethyl-7-benzofuranyloxy | 96–97 |
| 15 | 3,4-methylenedioxyphenoxy | 142.5–143.5 |
| 16 | 4-(N,N-diethylaminomethyl)-2,5-dimethylphenoxy | 88–89.5 |
| 17 | phenylseleno | 102.5–103.5 |
| 18 | 1 phenyl-2,2,2-tribromoethoxy | 56–59 |

The following examples demonstrate the practice of the present invention. The test organisms used in these examples, together with an identifying code which are in the tables to identify each organism, are as follows:

| | | | |
|---|---|---|---|
| AS = | Alternaria solani | PO = | Pyricularia oryzae |
| BC = | Botrytis cinerea | PU = | Pythium ultimum |
| CC = | Cladosporium cucumerinum | RS = | Rhizoctonia solani |
| EP = | Erysiphe polygoni | SF = | Sclerotinia fructicola |
| FS = | Fusarium solani | UP = | Uromyces phaseoli |
| HO = | Helminthosporium oryzae | VI = | Venturia inaequalis |
| PI = | Phytophthora infestans | | |

EXAMPLE 19

Spore Germination Tests

The test chemical was dissolved or suspended in acetone in an amount such that 0.8 ml of the resulting suspension or solution, mixed with 40 ml water agar produced a water agar solution containing 40, 10, 2.5 and 1 ppm of test chemical. The resulting agar solution, at 50° C., was then divided equally between two sterile petri dishes, each having four separated quadrants, and allowed to solidify. Three quadrants of each dish were flooded with 0.1 ml of a spore suspension in sterile water. Spores of two pathogens, Erysiphe polygoni and Uromyes phaseoli, from infected plant leaves, were brushed on the remaining two quadrants. The tests were then incubated 48 hours, at 24° C.

Readings were then taken and the percentage of germinated spores calculated. From this percentage, a spore germination rating was assigned as follows:

| % Germination | Rating |
|---|---|
| 0–10 | 0 |
| 10–40 | 1 |
| 40–60 | 2 |
| 60–80 | 3 |
| 80–100 | 4 |

Table I reports the inhibitory effect of these test compounds on spore germination. In Table I, the lower the numeral used as a rating, the more effective the compound.

EXAMPLE 20

Mycelial Growth Tests

Aliquots of previously prepared solutions of active ingredient in acetone were added to tubes containing 20 ml of sterile, melted potato dextrose agar that had been cooled to 50° C. to provide mixtures of 40, 20, 10, 5 and 2.5 ppm. The tubes were shaken to ensure thorough mixing of the chemical with the agar, and the mixture poured into petri dishes having 4 quadrants to solidify. Each quadrant was inoculated with a 4 mm diameter disc of agar containing mycelium of the test fungi and incubated at 25° C. for 72 to 144 hours, depending on the species being employed, during which the samples were alternately exposed to light for 12 hours and to darkness for 12 hours. Growth was measured at the end of the incubation period by measuring the diameter of each fungus colony. Two measurements of the diameter, perpendicular to each other, were taken and the values averaged. Data are reported as percent inhibition (%I) by the following formula:

$$\%I = \frac{\text{mm growth of check} - \text{mm growth of treated sample}}{\text{mm growth of check}}$$

The results reported in Table II indicate a high level of activity for the test compounds.

TABLE I
RESULTS OF IN VITRO SPORE GERMINATION INHIBITION TESTING

| CPD of Example | Conc. ppm | BC | PO | VI | AS | CC | PI | EP | UP |
|---|---|---|---|---|---|---|---|---|---|
| 3 | 40 | 0 | 0 | 0 | 0 | 0 | 0 | 0 | 0 |
|  | 10 | 3 | 0 | 0 | 1 | 0 | 0 | 4 | 0 |
|  | 2.5 | 4 | 3 | 1 | 1 | 4 | 4 | 4 | 0 |
|  | 1.0 | 4 | 4 | 2 | 4 | 4 | 4 | 4 | 4 |
| 4 | 40 | 0 | 0 | 0 | 0 | 0 | 0 | 0 | 0 |
|  | 10 | 0 | 0 | 3 | 0 | 0 | 0 | 0 | 1 |
|  | 2.5 | 4 | 2 | 3 | 4 | 4 | 0 | 1 | 0 |
|  | 1.0 | 4 | 4 | 4 | 4 | 4 | 2 | 1 | 4 |
| 5 | 40 | 0 | 0 | 0 | 0 | 0 | 0 | 1 | 2 |
|  | 10 | 4 | 0 | 0 | 4 | 0 | 0 | 1 | 2 |
|  | 2.5 | 4 | 4 | 4 | 4 | 4 | 1 | 4 | 2 |
|  | 1.0 | 4 | 4 | 4 | 4 | 4 | 4 | 4 | 4 |
| 6 | 40 | 0 | 0 | 0 | 0 | 0 | 0 | 1 | 0 |
|  | 10 | 4 | 0 | 0 | 2 | 0 | 1 | 2 | 0 |
|  | 2.5 | 4 | 4 | 4 | 4 | 0 | 2 | 4 | 4 |
|  | 1.0 | 4 | 4 | 4 | 4 | 4 | 3 | 4 | 4 |
| 7 | 40 | 4 | 0 | 0 | 4 | 0 | 0 | 0 | 0 |
|  | 10 | 4 | 0 | 0 | 4 | 0 | 0 | 0 | 0 |
|  | 2.5 | 4 | 4 | 0 | 4 | 0 | 0 | 0 | 0 |
|  | 1.0 | 4 | 4 | 4 | 4 | 0 | 4 | 4 | 4 |
| 8 | 40 | 0 | 0 | 0 | 0 | 0 | 0 | 0 | 0 |
|  | 10 | 0 | 0 | 0 | 4 | 0 | 0 | 1 | 0 |
|  | 2.5 | 0 | 0 | 0 | 4 | 0 | 3 | 0 | 0 |
|  | 1.0 | 3 | 0 | 0 | 4 | 0 | 4 | 0 | 0 |
| 9 | 40 | 0 | 0 | — | 0 | 0 | 0 | 0 | 0 |
|  | 10 | 4 | 3 | — | 4 | 0 | 0 | 4 | 0 |
|  | 2.5 | 4 | 3 | — | 4 | 0 | 0 | 4 | 0 |
|  | 1.0 | 4 | 4 | — | 4 | 4 | 4 | 4 | 4 |
| 10 | 40 | 3 | 0 | 0 | 4 | 0 | 0 | 4 | 0 |
|  | 10 | 4 | 0 | 0 | 4 | 0 | 3 | 4 | 0 |
|  | 2.5 | 4 | 0 | 1 | 4 | 0 | 3 | 4 | 4 |
|  | 1.0 | 4 | 4 | 4 | 4 | 2 | 4 | 4 | 4 |
| 11 | 40 | 2 | 0 | 0 | 0 | 0 | 0 | 4 | 0 |
|  | 10 | 4 | 0 | 0 | 4 | 0 | 3 | 4 | 0 |
|  | 2.5 | 4 | 3 | 0 | 4 | 2 | 3 | 4 | 0 |
|  | 1.0 | 4 | 4 | 4 | 4 | 4 | 4 | 4 | 4 |
| 12 | 40 | 4 | 0 | 0 | 4 | 0 | 0 | 0 | 0 |
|  | 10 | 4 | 1 | 1 | 4 | 0 | 0 | 4 | 0 |
|  | 2.5 | 4 | 1 | 1 | 4 | 0 | 0 | 4 | 0 |
|  | 1.0 | 0 | 0 | 0 | 2 | 0 | 0 | 0 | 0 |
| 13 | 40 | 0 | 0 | 0 | 0 | 0 | 0 | 0 | 0 |
|  | 10 | 0 | 0 | 0 | 0 | 0 | 0 | 1 | 0 |
|  | 2.5 | 4 | 0 | 1 | 4 | 1 | 3 | 1 | 0 |
|  | 1.0 | 4 | 1 | 4 | 4 | 4 | 4 | 1 | 3 |
| 14 | 40 | 0 | 0 | 0 | 0 | 0 | 0 | 0 | 0 |
|  | 10 | 4 | 4 | 0 | 4 | 0 | 0 | 2 | 2 |
|  | 2.5 | 4 | 4 | 4 | 4 | 0 | 2 | 2 | 2 |
|  | 1.0 | 4 | 4 | 4 | 4 | 4 | 4 | 4 | 4 |
| 15 | 40 | 0 | 0 | 0 | 0 | 0 | 2 | 4 | 0 |
|  | 10 | 3 | 0 | 0 | 1 | 0 | 1 | 4 | 0 |
|  | 2.5 | 4 | 1 | 1 | 3 | 0 | 2 | 4 | 2 |
|  | 1.0 | 4 | 4 | 3 | 4 | 1 | 4 | 4 | 4 |
| 16 | 40 | 4 | 0 | 4 | 0 | 0 | 4 | 4 | 1 |
|  | 10 | 4 | 4 | 4 | 4 | 2 | 4 | 4 | 4 |
|  | 2.5 | 4 | 4 | 4 | 4 | 4 | 4 | 4 | 4 |
|  | 1.0 | 4 | 4 | 4 | 4 | 4 | 4 | 0 | 4 |
| 17 | 40 | 0 | 0 | 0 | 0 | 0 | 0 | 0 | 0 |
|  | 10 | 0 | 0 | 0 | 0 | 0 | 1 | 0 | 0 |
|  | 2.5 | 0 | 0 | 0 | 0 | 0 | 2 | 0 | 0 |
|  | 1.0 | 0 | 0 | 0 | 2 | 0 | 2 | 0 | 0 |
| 18 | 40 | 0 | 0 | 0 | 0 | 0 | 0 | 0 | 0 |
|  | 10 | 0 | 0 | 0 | 0 | 0 | 0 | 0 | 0 |
|  | 2.5 | 1 | 0 | 0 | 2 | 0 | 1 | 0 | 0 |
|  | 1.0 | 4 | 0 | 0 | 4 | 0 | 0 | 1 | 0 |

TABLE II
RESULTS OF IN VITRO MYCELIAL GROWTH INHIBITION EVALUATION

| CPD of Ex. | Conc. ppm | AS | FS | SF | PO | PU | RS | HO | CC |
|---|---|---|---|---|---|---|---|---|---|
| 3 | 40 | 82 | 90 | 100 | 52 | 100 | 78 | 100 | 47 |
|  | 20 | 73 | 50 | 71 | 28 | 100 | 73 | 100 | 27 |
|  | 10 | 73 | 55 | 88 | 62 | 67 | 47 | 100 | 20 |
|  | 5 | 73 | 30 | 38 | 31 | 20 | 20 | 44 | 27 |
| 4 | 40 | 100 | 100 | 100 | 59 | 100 | 78 | 100 | 80 |
|  | 20 | 73 | 70 | 68 | 17 | 64 | 53 | 100 | 63 |
|  | 10 | 64 | 45 | 38 | 24 | 0 | 24 | 63 | 20 |
|  | 5 | 50 | 20 | 9 | 28 | 0 | 0 | 50 | 27 |
| 5 | 40 | 100 | 100 | 100 | 62 | 100 | 100 | 100 | 54 |
|  | 20 | 88 | 64 | 100 | 35 | 76 | 61 | 58 | 42 |
|  | 10 | 31 | 21 | 44 | 19 | 0 | 0 | 25 | 21 |
|  | 5 | 44 | 21 | 44 | 19 | 0 | 0 | 17 | 13 |
| 6 | 40 | 0 | 100 | 100 | 38 | 100 | 42 | 100 | 92 |
|  | 20 | 25 | 100 | 100 | 31 | 13 | 6 | 100 | 92 |
|  | 10 | 50 | 0 | 63 | 19 | 0 | 0 | 100 | 42 |
|  | 5 | 38 | 0 | 38 | 8 | 0 | 0 | 50 | 33 |
| 7 | 40 | 38 | 21 | 100 | 46 | 0 | 28 | 83 | 50 |
|  | 20 | 6 | 14 | 100 | 46 | 0 | 14 | 33 | 33 |
|  | 10 | 0 | 21 | 100 | — | 0 | 14 | 0 | 42 |
|  | 5 | 0 | 26 | 100 | 19 | 0 | 20 | 42 | 33 |
| 8 | 40 | 33 | 52 | 23 | 30 | 20 | 73 | 50 | 19 |
|  | 20 | 21 | 52 | 15 | 13 | 42 | 56 | 25 | 8 |
|  | 10 | 33 | 43 | 0 | 0 | 0 | 31 | 31 | 0 |
|  | 5 | 29 | 33 | 0 | 7 | 0 | 0 | 13 | 8 |
| 9 | 40 | 94 | 58 | 83 | 77 | 100 | 56 | 100 | 74 |
|  | 20 | 81 | 46 | 76 | 58 | 100 | 42 | 47 | 53 |
|  | 10 | 68 | 33 | 61 | 15 | 0 | 0 | 27 | 24 |
|  | 5 | 55 | 13 | 37 | 0 | 0 | 0 | 0 | 9 |
| 10 | 40 | 50 | 57 | 63 | 77 | 64 | 17 | 100 | 67 |
|  | 20 | 63 | 29 | 63 | 65 | 42 | 1 | 83 | 46 |
|  | 10 | 38 | 29 | 38 | 65 | 11 | 44 | 100 | 33 |
|  | 5 | 38 | 29 | 25 | 31 | 0 | 28 | 67 | 17 |
| 11 | 40 | 57 | 70 | 73 | 54 | 100 | 78 | 100 | 9 |
|  | 20 | 71 | 50 | 62 | 54 | 100 | 20 | 44 | 24 |
|  | 10 | 43 | 45 | 30 | 13 | 20 | 11 | 44 | 38 |
|  | 5 | 48 | 0 | 30 | 13 | 0 | 0 | 11 | 21 |
| 12 | 40 | 71 | 100 | 100 | 62 | 100 | 100 | 100 | 92 |
|  | 20 | 52 | 53 | 100 | 58 | 86 | 76 | 71 | 77 |
|  | 10 | 33 | 53 | 73 | 31 | 31 | 31 | 52 | 62 |
|  | 5 | 24 | 18 | 63 | 19 | 0 | 0 | 52 | 38 |
| 13 | 40 | 100 | 100 | 100 | 45 | 100 | 69 | 100 | 77 |
|  | 20 | 73 | 80 | 85 | 31 | 87 | 64 | 88 | 47 |
|  | 10 | 59 | 50 | 59 | 17 | 20 | 33 | 88 | 30 |
|  | 5 | 59 | 40 | 35 | 0 | 0 | 11 | 75 | 20 |
| 14 | 40 | 100 | 100 | 100 | 100 | 100 | 75 | 100 | 92 |
|  | 20 | 44 | 100 | 69 | 62 | 33 | 67 | 100 | 33 |
|  | 10 | 38 | 43 | 13 | 19 | 7 | 39 | 50 | 8 |
|  | 5 | 0 | 21 | 38 | 15 | 0 | 0 | 25 | 0 |
| 15 | 40 | 100 | 100 | 100 | 100 | 100 | 100 | 100 | 100 |
|  | 20 | 100 | 100 | 100 | 46 | 100 | 100 | 100 | 63 |
|  | 10 | 50 | 86 | 100 | 19 | 100 | 33 | 100 | 17 |
|  | 5 | 44 | 29 | 38 | 19 | 42 | 28 | 50 | 0 |
| 16 | 40 | 65 | 26 | 48 | 42 | 100 | 73 | 100 | 47 |

TABLE II-continued
RESULTS OF IN VITRO
MYCELIAL GROWTH INHIBITION EVALUATION

| CPD of Ex. | Conc. ppm. | Percent Fungus Growth Inhibition | | | | | | | |
|---|---|---|---|---|---|---|---|---|---|
| | | AS | FS | SF | PO | PU | RS | HO | CC |
| | 20 | 38 | 11 | 29 | 21 | 9 | 29 | 16 | 29 |
| | 10 | 38 | 0 | 23 | 13 | 0 | 0 | 0 | 24 |
| | 5 | 38 | 0 | 16 | 0 | 0 | 0 | 0 | 18 |
| 17 | 40 | 100 | 100 | 100 | 100 | 100 | 100 | 100 | 82 |
| | 20 | 100 | 100 | 100 | 100 | 71 | 87 | 100 | 53 |
| | 10 | 81 | 100 | 100 | 63 | 20 | 69 | 100 | 29 |
| | 5 | 71 | 100 | 100 | 67 | 0 | 69 | 100 | 24 |
| 18 | 40 | 90 | 8 | 84 | 42 | 0 | 76 | 100 | 42 |
| | 20 | 53 | 7 | 73 | 25 | 0 | 65 | 100 | 21 |
| | 10 | 11 | 45 | 57 | 0 | 0 | 42 | 44 | 15 |
| | 5 | 33 | 4 | 57 | 13 | 0 | 36 | 44 | 0 |

We claim:
1. A compound of the formula

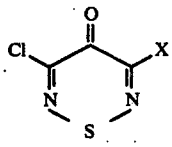

in which X is phenoxybenzyloxy, α-cyano-phenoxybenzyloxy, methylenedioxyphenoxy optionally substituted on the methylene with 1 or 2 lower alkyl groups, 2,3-dihydrobenzofuranyloxy optionally substituted at the 2 or 3 position of the furanyl ring with 1 or 2 lower alkyl groups, phenylseleno in which the phenyl ring is optionally substituted with 1 to 3 groups independently selected from lower alkyl and halogen, or substituted phenoxy having the formula

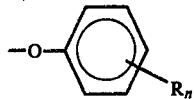

wherein n has a value of 1 to 3 inclusive, wherein at least one R group is halo(lower)alkyl, hydroxy(lower)alkyl, carboxyethenyl, lower alkoxycarbonylethenyl, dimethylamino, lower alkylamino ($C_{1-2}$)alkyl, lower alkylaminocarbonyloxy ($C_{1-2}$) alkyl, or phenylaminocarbonyloxy($C_{1-2}$)alkyl, and wherein the remaining R groups are independently selected from lower alkyl, halo, lower alkoxy, hydroxy, nitro, cyano, amino, carboxyl, lower acyl, lower acylamino, lower alkoxycarbonyl, carboxy(lower)alkyl, lower alkylureido, phenylureido, trihalomethyl, cyano(lower)alkyl, phenyl(lower)alkoxycarbonyloxy, lower alkylaminocarbonyloxy, phenylaminocarbonyloxy, lower alkylthio, lower alkylsulfinyl and lower alkylsulfonyl.

2. A fungicidal composition comprising the compound of claim 1 in admixture with an agriculturally acceptable carrier.

3. A method for controlling fungal disease in plants which comprises applying to the locus where control is desired an effective fungistatic or fungicidal amount of the compound of claim 1.

* * * * *

UNITED STATES PATENT AND TRADEMARK OFFICE
CERTIFICATE OF CORRECTION

PATENT NO. : 4,201,780
DATED : May 6, 1980
INVENTOR(S) : Clinton J. Peake; Wayne N. Harnish; Bruce L. Davidson It is certified that error appears in the above-identified patent and that said Letters Patent are hereby corrected as shown below:

Column 2, line 19, "lower alkanoylacylamino," should read --lower alkanoylamino,--. Column 4, line 36, "1.2,6-thiadiazin-4-one;" should read --1,2,6-thiadiazin-4-one;--; line 55, "(N-methylcarbamoyloxymethyl)phenoxyl]-4-H-1,2,6-" should read --(N-methylcarbamoyloxymethyl)phenoxyl]-4H-1,2,6---

Signed and Sealed this

Twenty-eighth Day of October 1980

[SEAL]

Attest:

SIDNEY A. DIAMOND

Attesting Officer

Commissioner of Patents and Trademarks